United States Patent
Inouye et al.

(10) Patent No.: US 8,476,037 B2
(45) Date of Patent: Jul. 2, 2013

(54) METHOD FOR SCREENING OF ANTIVIRAL AGENTS

(75) Inventors: Masayori Inouye, New Brunswick, NJ (US); Lili Mao, Piscataway, NJ (US); William F. Degrado, San Francisco, CA (US); Nathan H. Joh, San Francisco, CA (US)

(73) Assignees: University of Medicine and Dentistry of New Jersey, Somerset, NJ (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 13/213,230

(22) Filed: Aug. 19, 2011

(65) Prior Publication Data

US 2012/0045789 A1 Feb. 23, 2012

Related U.S. Application Data

(60) Provisional application No. 61/375,170, filed on Aug. 19, 2010.

(51) Int. Cl.
*C12Q 1/02* (2006.01)
(52) U.S. Cl.
USPC .......................................................... 435/29
(58) Field of Classification Search
None
See application file for complete search history.

(56) References Cited

U.S. PATENT DOCUMENTS

| 2009/0075270 A1 | 3/2009 | Cueva-Mendez et al. ... 435/6.11 |
| 2010/0035346 A1 | 2/2010 | Inouye et al. .................. 435/471 |
| 2011/0065762 A1* | 3/2011 | Wang et al. .................... 514/375 |

OTHER PUBLICATIONS

Gervais C. et al. Development and Validation of a High Throughput Screening Assay for the Hepatitis C Virus p7 Viroporin. Journal of Biomoelcular Screening 16(3)363-369, Feb. 2011.*
Madan V. et al. Viroporin Activity of Murine Hepatitis Virus E Protein. FEBS Letters 579:3607-3612, 2005.*
Suzuki et al. "Single Protein Production in Living Cells Facilitated by an mRNA Interferase" Molecular Cell 2005 vol. 18:253-261.
Suzuki et al. "Bacterial Bioreactors for High Yield Production of Recombinant Protein" The Journal of Biological Chemistry 2006 vol. 281(49):37559-37565.
Zhang et al. "MazF Cleaves Cellular mRNAs Specifically at ACA to Block Protein Synthesis in *Escherichia coli*" Molecular Cell 2003 vol. 12:913-923.

* cited by examiner

*Primary Examiner* — Ralph Gitomer
(74) *Attorney, Agent, or Firm* — Licata & Tyrrell P.C.

(57) ABSTRACT

A method for screening for an antiviral agent capable of blocking a viral viroporin by determining whether a test agent can rescue expression of a fragment of a viral viroporin in a Single Protein Production system of *Escherichia coli* is provided.

2 Claims, No Drawings

SEQUENCE LISTING

```
<160> NUMBER OF SEQ ID NOS: 11

<210> SEQ ID NO 1
<211> LENGTH: 49
<212> TYPE: PRT
<213> ORGANISM: Influenza A virus
<220> FEATURE:
```

-continued

```
<221> NAME/KEY: MISC_FEATURE
<222> LOCATION: (21)..(21)
<223> OTHER INFORMATION: Xaa denotes Asp or Gly
<220> FEATURE:
<221> NAME/KEY: MISC_FEATURE
<222> LOCATION: (26)..(26)
<223> OTHER INFORMATION: Xaa denotes Leu or Phe
<220> FEATURE:
<221> NAME/KEY: MISC_FEATURE
<222> LOCATION: (27)..(27)
<223> OTHER INFORMATION: Xaa denotes Val or Ala
<220> FEATURE:
<221> NAME/KEY: MISC_FEATURE
<222> LOCATION: (28)..(28)
<223> OTHER INFORMATION: Xaa denotes Ile or Val
<220> FEATURE:
<221> NAME/KEY: MISC_FEATURE
<222> LOCATION: (31)..(31)
<223> OTHER INFORMATION: Xaa denotes Ser or Asn
<220> FEATURE:
<221> NAME/KEY: MISC_FEATURE
<222> LOCATION: (38)..(38)
<223> OTHER INFORMATION: Xaa denotes Leu or Phe
<220> FEATURE:
<221> NAME/KEY: MISC_FEATURE
<222> LOCATION: (39)..(39)
<223> OTHER INFORMATION: Xaa denotes Ile or Thr
<220> FEATURE:
<221> NAME/KEY: MISC_FEATURE
<222> LOCATION: (45)..(45)
<223> OTHER INFORMATION: Xaa denotes Arg or His

<400> SEQUENCE: 1

Met Ser Leu Leu Thr Glu Val Glu Thr Pro Ile Arg Asn Glu Trp Gly
1               5                   10                  15

Cys Arg Cys Asn Xaa Ser Ser Asp Pro Xaa Xaa Xaa Ala Ala Xaa Ile
            20                  25                  30

Ile Gly Ile Leu His Xaa Xaa Leu Trp Ile Leu Asp Xaa Leu Phe Phe
        35                  40                  45

Lys

<210> SEQ ID NO 2
<211> LENGTH: 49
<212> TYPE: PRT
<213> ORGANISM: Influenza A virus
<220> FEATURE:
<221> NAME/KEY: MISC_FEATURE
<222> LOCATION: (10)..(10)
<223> OTHER INFORMATION: Xaa denotes Pro, Leu or His
<220> FEATURE:
<221> NAME/KEY: MISC_FEATURE
<222> LOCATION: (13)..(13)
<223> OTHER INFORMATION: Xaa denotes Asn or Ser
<220> FEATURE:
<221> NAME/KEY: MISC_FEATURE
<222> LOCATION: (18)..(18)
<223> OTHER INFORMATION: Xaa denotes Lys, Arg or Ser
<220> FEATURE:
<221> NAME/KEY: MISC_FEATURE
<222> LOCATION: (19)..(19)
<223> OTHER INFORMATION: Xaa denotes Cys or Tyr
<220> FEATURE:
<221> NAME/KEY: MISC_FEATURE
<222> LOCATION: (20)..(20)
<223> OTHER INFORMATION: Xaa denotes Asn or Ser
<220> FEATURE:
<221> NAME/KEY: MISC_FEATURE
<222> LOCATION: (27)..(27)
<223> OTHER INFORMATION: Xaa denotes Val or Ile
<220> FEATURE:
<221> NAME/KEY: MISC_FEATURE
<222> LOCATION: (38)..(38)
<223> OTHER INFORMATION: Xaa denotes Leu or Phe
<220> FEATURE:
<221> NAME/KEY: MISC_FEATURE
```

```
<222> LOCATION: (43)..(43)
<223> OTHER INFORMATION: Xaa denotes Leu or Phe
<220> FEATURE:
<221> NAME/KEY: MISC_FEATURE
<222> LOCATION: (44)..(44)
<223> OTHER INFORMATION: Xaa denotes Asp, Tyr, or Asn

<400> SEQUENCE: 2

Met Ser Leu Leu Thr Glu Val Glu Thr Xaa Thr Arg Xaa Gly Trp Glu
1               5                   10                  15

Cys Xaa Xaa Xaa Asp Ser Ser Asp Pro Leu Xaa Ile Ala Ala Ser Ile
            20                  25                  30

Ile Gly Ile Leu His Xaa Ile Leu Trp Ile Xaa Xaa Arg Leu Phe Phe
        35                  40                  45

Lys

<210> SEQ ID NO 3
<211> LENGTH: 49
<212> TYPE: PRT
<213> ORGANISM: Influenza A virus
<220> FEATURE:
<221> NAME/KEY: MISC_FEATURE
<222> LOCATION: (11)..(11)
<223> OTHER INFORMATION: Xaa denotes Thr or Ile
<220> FEATURE:
<221> NAME/KEY: MISC_FEATURE
<222> LOCATION: (13)..(13)
<223> OTHER INFORMATION: Xaa denotes Asn or Ser
<220> FEATURE:
<221> NAME/KEY: MISC_FEATURE
<222> LOCATION: (18)..(18)
<223> OTHER INFORMATION: Xaa denotes Lys or Arg
<220> FEATURE:
<221> NAME/KEY: MISC_FEATURE
<222> LOCATION: (29)..(29)
<223> OTHER INFORMATION: Xaa denotes Val or Ala

<400> SEQUENCE: 3

Met Ser Leu Leu Thr Glu Val Glu Thr Pro Xaa Arg Xaa Glu Trp Gly
1               5                   10                  15

Cys Xaa Cys Asn Asp Ser Ser Asp Pro Leu Val Ala Xaa Ala Ser Ile
            20                  25                  30

Ile Gly Ile Leu His Leu Ile Leu Trp Ile Leu Asp Arg Leu Phe Phe
        35                  40                  45

Lys

<210> SEQ ID NO 4
<211> LENGTH: 31
<212> TYPE: PRT
<213> ORGANISM: Influenza B virus

<400> SEQUENCE: 4

Met Leu Glu Pro Phe Gln Ile Leu Ser Ile Cys Ser Phe Ile Leu Ser
1               5                   10                  15

Ala Leu His Phe Met Ala Trp Thr Ile Gly His Leu Asn Gln Ile
            20                  25                  30

<210> SEQ ID NO 5
<211> LENGTH: 51
<212> TYPE: PRT
<213> ORGANISM: Influenza C virus

<400> SEQUENCE: 5

Cys Asn Leu Lys Thr Cys Leu Lys Leu Phe Asn Asn Thr Asp Ala Val
1               5                   10                  15
```

```
Thr Val His Cys Phe Asn Glu Asn Gln Gly Tyr Met Leu Thr Leu Ala
        20                  25                  30

Ser Leu Gly Leu Gly Ile Ile Thr Met Leu Tyr Leu Leu Val Lys Ile
            35                  40                  45

Ile Ile Glu
    50

<210> SEQ ID NO 6
<211> LENGTH: 62
<212> TYPE: PRT
<213> ORGANISM: Ross River virus

<400> SEQUENCE: 6

Gly Ser Ala Ser Phe Ala Glu Thr Met Ala Tyr Leu Trp Asp Glu Asn
1               5                   10                  15

Lys Thr Leu Phe Trp Met Glu Phe Ala Ala Pro Ala Ala Leu Ala
            20                  25                  30

Leu Leu Ala Cys Cys Ile Lys Ser Leu Ile Cys Cys Lys Pro Phe
            35                  40                  45

Ser Phe Leu Val Leu Leu Ser Leu Gly Ala Ser Ala Lys Ala
    50                  55                  60

<210> SEQ ID NO 7
<211> LENGTH: 55
<212> TYPE: PRT
<213> ORGANISM: Barmah Forest virus

<400> SEQUENCE: 7

Gly Ser Asp Thr Leu Asp Asp Phe Ser Tyr Leu Trp Thr Asn Asn Gln
1               5                   10                  15

Ala Met Phe Trp Leu Gln Leu Ala Ser Pro Val Ala Ala Phe Leu Cys
            20                  25                  30

Leu Ser Tyr Cys Cys Arg Asn Leu Ala Cys Cys Met Lys Ile Phe Leu
            35                  40                  45

Gly Ile Ser Gly Leu Cys Val
    50                  55

<210> SEQ ID NO 8
<211> LENGTH: 51
<212> TYPE: PRT
<213> ORGANISM: Sindbis virus

<400> SEQUENCE: 8

Glu Thr Phe Thr Glu Thr Met Ser Tyr Leu Trp Ser Asn Ser Gln Pro
1               5                   10                  15

Phe Phe Trp Val Gln Leu Cys Ile Pro Leu Ala Ala Phe Ile Val Leu
            20                  25                  30

Met Arg Cys Cys Ser Cys Cys Leu Pro Phe Leu Val Val Ala Gly Ala
            35                  40                  45

Tyr Leu Ala
    50

<210> SEQ ID NO 9
<211> LENGTH: 33
<212> TYPE: PRT
<213> ORGANISM: Human immunodeficiency virus type 1

<400> SEQUENCE: 9

Met Gln Pro Ile Pro Ile Val Ala Ile Val Ala Leu Val Val Ala Ile
1               5                   10                  15
```

Ile Ile Ala Ile Val Val Trp Ser Ile Val Ile Ile Glu Tyr Arg Lys
          20                  25                  30

Ile

<210> SEQ ID NO 10
<211> LENGTH: 47
<212> TYPE: PRT
<213> ORGANISM: Human respiratory syncytial virus
<220> FEATURE:
<221> NAME/KEY: MISC_FEATURE
<222> LOCATION: (21)..(21)
<223> OTHER INFORMATION: Xaa denotes Ile, Thr or Val
<220> FEATURE:
<221> NAME/KEY: MISC_FEATURE
<222> LOCATION: (22)..(22)
<223> OTHER INFORMATION: Xaa denotes His or Phe
<220> FEATURE:
<221> NAME/KEY: MISC_FEATURE
<222> LOCATION: (24)..(24)
<223> OTHER INFORMATION: Xaa denotes Ile or Met
<220> FEATURE:
<221> NAME/KEY: MISC_FEATURE
<222> LOCATION: (25)..(25)
<223> OTHER INFORMATION: Xaa denotes Leu or Thr
<220> FEATURE:
<221> NAME/KEY: MISC_FEATURE
<222> LOCATION: (26)..(26)
<223> OTHER INFORMATION: Xaa denotes Thr or Ile
<220> FEATURE:
<221> NAME/KEY: MISC_FEATURE
<222> LOCATION: (27)..(27)
<223> OTHER INFORMATION: Xaa denotes Leu, Ile or Pro
<220> FEATURE:
<221> NAME/KEY: MISC_FEATURE
<222> LOCATION: (28)..(28)
<223> OTHER INFORMATION: Xaa denotes Ile or Gly
<220> FEATURE:
<221> NAME/KEY: MISC_FEATURE
<222> LOCATION: (29)..(29)
<223> OTHER INFORMATION: Xaa denotes Ser or Phe
<220> FEATURE:
<221> NAME/KEY: MISC_FEATURE
<222> LOCATION: (30)..(30)
<223> OTHER INFORMATION: Xaa denotes Leu or Phe
<220> FEATURE:
<221> NAME/KEY: MISC_FEATURE
<222> LOCATION: (31)..(31)
<223> OTHER INFORMATION: Xaa denotes Leu, Phe or Val
<220> FEATURE:
<221> NAME/KEY: MISC_FEATURE
<222> LOCATION: (32)..(32)
<223> OTHER INFORMATION: Xaa denotes Ile or Val
<220> FEATURE:
<221> NAME/KEY: MISC_FEATURE
<222> LOCATION: (33)..(33)
<223> OTHER INFORMATION: Xaa denotes Ile, Thr or Val
<220> FEATURE:
<221> NAME/KEY: MISC_FEATURE
<222> LOCATION: (34)..(34)
<223> OTHER INFORMATION: Xaa denotes Ile or Thr
<220> FEATURE:
<221> NAME/KEY: MISC_FEATURE
<222> LOCATION: (35)..(35)
<223> OTHER INFORMATION: Xaa denotes Ser or Thr
<220> FEATURE:
<221> NAME/KEY: MISC_FEATURE
<222> LOCATION: (36)..(36)
<223> OTHER INFORMATION: Xaa denotes Ile or Leu
<220> FEATURE:
<221> NAME/KEY: MISC_FEATURE
<222> LOCATION: (37)..(37)
<223> OTHER INFORMATION: Xaa denotes Met or Val
<220> FEATURE:
<221> NAME/KEY: MISC_FEATURE
<222> LOCATION: (38)..(38)
<223> OTHER INFORMATION: Xaa denotes Ile, Thr or Ala
<220> FEATURE:
<221> NAME/KEY: MISC_FEATURE

```
<222> LOCATION: (40)..(40)
<223> OTHER INFORMATION: Xaa denotes Val or Ile

<400> SEQUENCE: 10

Met Glu Asn Thr Ser Ile Thr Ile Glu Phe Ser Ser Lys Phe Trp Pro
1               5                   10                  15

Tyr Phe Thr Leu Xaa Xaa Met Xaa Xaa Xaa Xaa Xaa Xaa Xaa Xaa Xaa
                20                  25                  30

Xaa Xaa Xaa Xaa Xaa Xaa Ala Xaa Leu Asn Lys Leu Cys Glu Tyr
            35                  40                  45

<210> SEQ ID NO 11
<211> LENGTH: 63
<212> TYPE: PRT
<213> ORGANISM: Hepatitis C virus
<220> FEATURE:
<221> NAME/KEY: MISC_FEATURE
<222> LOCATION: (4)..(4)
<223> OTHER INFORMATION: Xaa denotes Asn or Lys
<220> FEATURE:
<221> NAME/KEY: MISC_FEATURE
<222> LOCATION: (7)..(7)
<223> OTHER INFORMATION: Xaa denotes Ile, Val or Ala
<220> FEATURE:
<221> NAME/KEY: MISC_FEATURE
<222> LOCATION: (13)..(13)
<223> OTHER INFORMATION: Xaa denotes Leu, Val or Ala
<220> FEATURE:
<221> NAME/KEY: MISC_FEATURE
<222> LOCATION: (15)..(15)
<223> OTHER INFORMATION: Xaa denotes Gly or Ser
<220> FEATURE:
<221> NAME/KEY: MISC_FEATURE
<222> LOCATION: (16)..(16)
<223> OTHER INFORMATION: Xaa denotes Thr, Ala or Cys
<220> FEATURE:
<221> NAME/KEY: MISC_FEATURE
<222> LOCATION: (17)..(17)
<223> OTHER INFORMATION: Xaa denotes His or Asn
<220> FEATURE:
<221> NAME/KEY: MISC_FEATURE
<222> LOCATION: (19)..(19)
<223> OTHER INFORMATION: Xaa denotes Leu, Ile or Phe
<220> FEATURE:
<221> NAME/KEY: MISC_FEATURE
<222> LOCATION: (20)..(20)
<223> OTHER INFORMATION: Xaa denotes Val or Leu
<220> FEATURE:
<221> NAME/KEY: MISC_FEATURE
<222> LOCATION: (21)..(21)
<223> OTHER INFORMATION: Xaa denotes Ser or Tyr
<220> FEATURE:
<221> NAME/KEY: MISC_FEATURE
<222> LOCATION: (23)..(23)
<223> OTHER INFORMATION: Xaa denotes Leu or Val
<220> FEATURE:
<221> NAME/KEY: MISC_FEATURE
<222> LOCATION: (24)..(24)
<223> OTHER INFORMATION: Xaa denotes Val or Ile
<220> FEATURE:
<221> NAME/KEY: MISC_FEATURE
<222> LOCATION: (27)..(27)
<223> OTHER INFORMATION: Xaa denotes Cys or Val
<220> FEATURE:
<221> NAME/KEY: MISC_FEATURE
<222> LOCATION: (28)..(28)
<223> OTHER INFORMATION: Xaa denotes Phe or Ala
<220> FEATURE:
<221> NAME/KEY: MISC_FEATURE
<222> LOCATION: (32)..(32)
<223> OTHER INFORMATION: Xaa denotes Leu or Ile
<220> FEATURE:
<221> NAME/KEY: MISC_FEATURE
<222> LOCATION: (36)..(36)
<223> OTHER INFORMATION: Xaa denotes Trp or Leu
<220> FEATURE:
```

```
<221> NAME/KEY: MISC_FEATURE
<222> LOCATION: (37)..(37)
<223> OTHER INFORMATION: Xaa denotes Val or Ala
<220> FEATURE:
<221> NAME/KEY: MISC_FEATURE
<222> LOCATION: (39)..(39)
<223> OTHER INFORMATION: Xaa denotes Gly or Leu
<220> FEATURE:
<221> NAME/KEY: MISC_FEATURE
<222> LOCATION: (41)..(41)
<223> OTHER INFORMATION: Xaa denotes Val, Ala or Thr
<220> FEATURE:
<221> NAME/KEY: MISC_FEATURE
<222> LOCATION: (43)..(43)
<223> OTHER INFORMATION: Xaa denotes Ala or Ser
<220> FEATURE:
<221> NAME/KEY: MISC_FEATURE
<222> LOCATION: (44)..(44)
<223> OTHER INFORMATION: Xaa denotes Phe or Leu
<220> FEATURE:
<221> NAME/KEY: MISC_FEATURE
<222> LOCATION: (45)..(45)
<223> OTHER INFORMATION: Xaa denotes Tyr or Thr
<220> FEATURE:
<221> NAME/KEY: MISC_FEATURE
<222> LOCATION: (47)..(47)
<223> OTHER INFORMATION: Xaa denotes Met, Val, Ala or Leu
<220> FEATURE:
<221> NAME/KEY: MISC_FEATURE
<222> LOCATION: (49)..(49)
<223> OTHER INFORMATION: Xaa denotes Pro or Ser
<220> FEATURE:
<221> NAME/KEY: MISC_FEATURE
<222> LOCATION: (50)..(50)
<223> OTHER INFORMATION: Xaa denotes Leu or Phe
<220> FEATURE:
<221> NAME/KEY: MISC_FEATURE
<222> LOCATION: (51)..(51)
<223> OTHER INFORMATION: Xaa denotes Leu or Ser
<220> FEATURE:
<221> NAME/KEY: MISC_FEATURE
<222> LOCATION: (56)..(56)
<223> OTHER INFORMATION: Xaa denotes Ala or Thr
<220> FEATURE:
<221> NAME/KEY: MISC_FEATURE
<222> LOCATION: (59)..(59)
<223> OTHER INFORMATION: Xaa denotes Gln or Pro
<220> FEATURE:
<221> NAME/KEY: MISC_FEATURE
<222> LOCATION: (60)..(60)
<223> OTHER INFORMATION: Xaa denotes Gln or Arg

<400> SEQUENCE: 11

Ala Leu Glu Xaa Leu Val Xaa Leu Asn Ala Ala Ser Xaa Ala Xaa Xaa
1               5                   10                  15

Xaa Gly Xaa Xaa Xaa Phe Xaa Xaa Phe Phe Xaa Xaa Ala Trp Tyr Xaa
            20                  25                  30

Lys Gly Arg Xaa Xaa Pro Xaa Ala Xaa Tyr Xaa Xaa Xaa Gly Xaa Trp
        35                  40                  45

Xaa Xaa Xaa Leu Leu Leu Leu Xaa Leu Pro Xaa Xaa Ala Tyr Ala
    50                  55                  60
```

METHOD FOR SCREENING OF ANTIVIRAL AGENTS

INTRODUCTION

This application claims priority to U.S. Provisional Application No. 61/375,170, filed Aug. 19, 2010, which is incorporated herein by reference in its entirety.

BACKGROUND OF THE INVENTION

The surface membrane proteins of the influenza virus A is composed of three important components, hemagglutinin, neuraminidase, and the M2 channel (Jong, et al. (2006) *J. Clin. Virol.* 35:2-13), which is a member of the class of proteins termed "viroporins" (Gonzalez & Carrasco (2003) *FEBS Lett.* 552:28-34). The M2 channel is a homotetrameric protein composed of 97 residues per subunit. Each subunit includes an extracellular N-terminal domain (24 residues), a transmembrane (TM) domain (19 residues), and an intracellular C-terminal domain (54 residues) (Lamb, et al. (1985) *Cell* 40:627-633; Holsinger & Lamb (1991) *Virology* 183:32-43; Sugrue & Hay (1991) *Virology* 180:617-624). The viral M2 protein functions as a proton selective channel, which is activated by low pH environments as found in endosomes (Sakaguchi, et al. (1997) *Proc. Natl. Acad. Sci. USA* 94:5000-5005). The main functional machinery of the proton-selective M2 channel is believed to lie within the TM helical bundle that exhibits proton conductive activity (Duff & Ashley (1992) *Virology* 190:485-489).

Amantadine (1-aminoadamantane hydrochloride) and rimantadine (α-methyl-1-adamantane methylamine hydrochloride), an amantadine analogue, are commercial drugs used for the prophylaxis and treatment of influenza A (Oxford, et al. (1980) *Pharmacol. Ther.* 11:181-262; Dollin, et al. (1982) *New Engl. J. Med.* 307:580-584) by inhibiting the ion-channel activity of the M2 protein (Pinto, et al. (1992) *Cell* 517-528; Sugrue & Hay (1991) *J. Virol.* 180:617-624; Hay (1992) *Semin. Virol.* 3:21-30). There have been several mechanisms suggested for how the inhibitors interact with the M2 protein. For example, it has been suggested that the inhibitors behave as 'blockers' (Hay, et al. (1992) supra; Sansom & Kerr (1993) *Prot. Eng.* 65-74; Duff, et al. (1994) *Virology* 202:287-293). In this view, the adamantyl group interacts with Asp24 and Val27 via van der Waals interactions, while the charged amine group hydrogen bonds with Ser31. Alternatively, is has been suggested that amantadine binds to a location deeper in the channel and its ammonium group hydrogen bonds with the His37 side chain (Pinto, et al. (1997) supra; Gandi, et al. (1999) *J. Biol. Chem.* 274:5474-5482). In this model, binding of the drug blocks proton channel activity by displacing water molecules that are essential for proton conduction. In support of both models, molecular dynamics simulations on the six possible His37 protonation states of M2 in free form and complexed with amantadine and rimantadine indicates that water density in the channel is reduced by the inhibitors (Intharathep, et al. (2008) *J. Mol. Graph. Model.* 27:342-348).

The emergence of resistance to amantadine in influenza A viruses has been shown to occur rapidly during treatment as a result of single-amino-acid substitutions at position 26, 27, 30, 31, or 34 within the transmembrane domain of the M2 protein (Klimov, et al. (1995) *J. Infect. Dis.* 172:1352-1355; Shiraishi, et al. (2003) *J. Infect. Dis.* 188:57-61). Therefore, there is a need in the art for new drugs to counter the emerging drug resistance. However, one of the major hindrances to the identification and development of antiviral compounds is the lack of suitable models for evaluating compounds with antiviral activity.

SUMMARY OF THE INVENTION

The present invention features a method for screening for an antiviral agent capable of blocking a viral viroporin. The method of the invention includes the steps of inducing expression of a viral viroporin fragment in a Single Protein Production system of *Escherichia coli* (*E. coli*); contacting the *E. coli* with a test compound; and determining whether expression of the viral viroporin fragment is rescued, wherein rescue of the expression of the viral viroporin fragment indicates that the compound blocks the viral viroporin. In some embodiments, the step of determining whether expression of the viral viroporin fragment is rescued includes the use of a reporter protein.

DETAILED DESCRIPTION OF THE INVENTION

It was observed that recombinant expression of the channel forming segment of the M2 protein, M2(1-49), in the condensed Single Protein Production (cSPP) system of *Escherichia coli* did not produce the expected ~5 kD peptide. It has now been found that the expression of M2(1-49) can be rescued with the addition of amantadine. Accordingly, this system is of use as a very effective high throughput drug screening assay for the identification of antiviral agent capable of blocking a viral viroporin.

Not wishing to be bound by theory, it is believed that since the expression of a proton channel protein would destroy the proton gradient across the *E. coli* membrane, inhibitors that block the channel rescue the expression of M2(1-49). Therefore, in addition to M2, this simple high throughput screening method for antiviral drugs is applicable to all viruses which form such ion channels across the membrane, including, e.g., Hepatitis C virus (p7), Bluetongue virus (NS3) and Ebola virus (V40).

Therefore, the present invention includes the use of fragments of viroporins in the identification of antiviral agents. In particular, the present invention embraces the use of a viroporin fragment comprising or consisting essentially of the N-terminal and membrane spanning domains of viroporins, which is capable of forming an ion channel. The viroporin fragments used in the instant method can vary in length depending on the viroporin employed. For example, the predicted membrane spanning domains of influenza A virus M2 and influenza B virus BM2 proton channels are 20 amino acids long, whereas the mature N-terminal domains are 23 and 6-7 amino acid residues, respectively (Pinto & Lamb (2006) *Photochem. Photobiol. Sci.* 5:629-632; Mould, et al. (20030 *Dev. Cell* 5:175-184). Similarly, the transmembrane domain of influenza C virus CM2 is 20 amino acid residues long (Kukol & Arkin (2000) *J. Biol. Chem.* 275:4225-4229) and the N-terminal domain is 26 amino acid residues after cleavage of the signal sequence (Pekosz & Lamb (1998) *Proc. Natl. Acad. Sci. USA* 95:13233-13238). In certain embodiments, the viroporin fragment is a fragment of the p7 peptide of Hepatitis C Virus (HCV); the nonstructural NS3 peptide of Bluetongue Virus; the V40 peptide of Ebola Virus; the M2 peptide of Influenza A Virus; the BM2 peptide of Influenza B Virus; the CM2 peptide of Influenza C Virus; the 6K peptide of alphaviruses such as Ross River Virus, Barmah Forest Virus (BFV), or Sindbis Virus; the Viral Protein U (Vpu) peptide of Human Immunodeficiency Virus Type 1 (HIV-1), and the Small Hydrophobic (SH) peptide of Human Respiratory Syncytial Virus (HRSV).

Representative fragments of viroporins of use in the instant invention are listed in Table 1.

TABLE 1

| Virus | Viro-N-terminal and Transmembrane porinDomains* | SEQ ID NO: |
|---|---|---|
| Human Influenza A Virus | M2 | MSLLTEVETPIRNEWGCRCN(D/G)SSDP(L/F)(V/A)(I/V)AA(S/N)IIGILH(L/F)(I/T)LWILD(R/H)LFFK [a,b] | 1 |
| Avian Influenza A Virus | M2 | MSLLTEVET(P/L/H)TR(N/S)GWEC(K/R/S)(C/Y)(S/N)DSSDPL(V/I)IAASIIGILH(L/F)ILWI(L/F)(D/Y/N)RLEFK [a,c] | 2 |
| Swine Influenza A Virus | M2 | MSLLTEVETP(T/I)R(S/N)EWGC(K/R)CNDSSDPLVA(V/A)ASIIGILHLILWILDRLFFK [a,d] | 3 |
| Influenza B Virus | BM2 | MLEPFQILSICSFILSALHFMAWTIGHLNQI | 4 |
| Influenza C Virus | CM2 | CNLKTCLKLFNNTDAVTVHCFNENQGYMLTLASLGLGIITMLYLLVKIIIE | 5 |
| Ross River Virus | 6K | GSASFAETMAYLWDENKTLFWMEFAAPAAALALLACCIKSLICCCKPFSFLVLLSLGASAKA [e] | 6 |
| BFV | 6K | GSDTLDDFSYLWTNNQAMFWLQLASPVAAFLCLSYCCRNLACCMKIFLGISGLCV [e] | 7 |
| Sindbis Virus | 6K | ETFTETMSYLWSNSQPFFWVQLCIPLAAFIVLMRCCSCCLPFLVVAGAYLA [f] | 8 |
| HIV-1 | Vpu | MQPIPIVAIVALVVAIIIAIVVWSIVIIEYRKI | 9 |
| HRSV | SH | MENTSITIEFSSKFWPYFTL(I/T/V)(H/F)M(I/M)(L/T)(T/I)(L/I/P)(I/G)(S/F)(L/F)(L/F/V)(I/V)(I/T/V)(I/T)(S/T)(I/L)(M/V)(I/T/A)A(V/I)LNKLCEY [g] | 10 |
| HCV | p7 | ALE(N/K)LV(I/V/A)LNAAS(L/V/A)A(G/S)(T/A/C)(H/N)G(L/I/F)(V/L)(S/Y)F(L/V)(V/I)FF(C/V)(F/A)AWY(L/I)KGR(W/L)(V/A)P(G/L)A(V/A/T)Y(A/S)(F/L)(Y/T)G(M/V/A/L)W(P/S)(L/F)(L/S)LLLL(A/T)LP(Q/P)(R/Q)AYA [h] | 11 |

*Underlined sequence represents the transmembrane domain.
[a]Ito, et al. (1991) J. Virol. 65: 5491-98.
[b]Consensus sequence of M2 peptides from A/WS/33 (H1N1), A/WSN/33 (H1N1), A/Fort Warren/1/50 (H1N1), A/USSR/90/77 (H1N1), A/Singapore/1/57 (H2N2), A/Ann Arbor/6/60 (H2N2), A/Korea/426/68 (H2N2), A/Aichi/2/68 (H3N2), A/Udorn/307/72 (H3N2), A/Port Chalmers/1/73 (H3N2), A/Bangkok/1/79 (H3N2), A/Memphis/8/88 (H3N2).
[c]Consensus sequence of M2 peptides from A/Chicken/Victoria/1/85 (H7N7), A/Duck/Czechoslovakia/56 (H4N6), A/FPV/Weybridge/27 (H7N7), A/FPV/Rostock/34 (H7N1), A/Chicken/Pennsylvania/1370/83 (H5N2), A/Chicken/Pennsylvania/1/83 (H5N2), A/Turkey/Minnesota/833/80 (H4N2), A/FPV/Weybridge/27 (H7N7), A/FPV/Rostock/34 (H7N1), A/Chicken/Pennsylvania/1370/83 (H5N2), A/Chicken/Pennsylvania/1/83 (H5N2), A/Turkey/Minnesota/833/80 (H4N2).
[d]Consensus sequence of M2 peptides from A/Swine/29/37 (H1N1), A/Swine/March/52 (H1N1), A/Swine/May/54 (H1N1), A/Swine/Wisconsin/1/61 (H1N1), A/Swine/Tennessee/24/77 (H1N 1), A/Swine/Ontario/2/81 (H1N1), A/Swine/Iowa/17672/88 (H1N1).
[e]Melton, et al. (2002) J. Biol. Chem. 277: 46923-46931.
[f]Sanz, et al. (2002) J. Biol. Chem. 278: 2051-2057.
[g]Consensus sequence of human RSV SH peptides from GENBANK Accession Nos AAG28111, AAG28084, VSHHRSV1, NP044594, AAG28086, AAG28139, AAG28127, AAG28107, AAX23992, BAA00813, AAG32979, AAG32979, AAG32970, and AAG32982; Gan, et al. (2008) Prot. Sci. 17: 813-820.
[h]Consensus sequence of p7 peptides from infectious HCV clones J4, H77, N, Con1, and J6; Griffin, et al. (2004) J. Gen. Virol. 85: 451-461).

In particular embodiments, the viroporin has one transmembrane domain. In another embodiment, the viroporin is homo-oligomeric. In a further embodiment, the viroporin is from an Influenza Virus. In particular embodiments, the viroporin is from Influenza A Virus.

Given that certain viroporins are translated with a signal peptide (e.g., CM2), the instant fragments can be recombinantly produced as mature peptides, i.e., without the native signal sequence. To facilitate translation, the codon for an initiator methionine can be included at the N-terminus of the viroporin, if not present in the mature peptide. Moreover, in addition to the N-terminal and transmembrane domain sequences, the instant viroporin fragments can include 0, 1, 2, 3, 4, 5, 6, or 7 residues located downstream of the transmembrane domain, i.e., additional C-terminal residues. Such modifications are routinely carried out in the art and can be carried out by conventional cloning or PCR methodology.

For use in the instant method, the nucleotide sequence encoding a viroporin fragment of interest is cloned or introduced into a vector suitable for expressing the viroporin fragment via the well-known Single Protein Production (SSP) system or condensed Single Protein Production (cSPP) of E. coli (Zhang, et al. (2003) Mol. Cell 12:913-23; Suzuki, et al. (2005) Mol. Cell 18:253-261; Suzuki, et al. (2006) J. Biol. Chem. 281:37559-65; US 2010/0035346; and US 2009/0075270), wherein background (non-specific) protein production is dramatically reduced or eliminated so as to generate a "single-protein". In order to construct a single-protein synthesizing system, the system is pretreated with an mRNA interferase (e.g., Kid, PemK and/or MazF), which cleaves endogenous mRNAs to block protein synthesis from these mRNAs. To effect such pretreatment in vivo, a regulatable gene for an mRNA interferase is introduced into a cell or tissue and its expression induced. Methods for introducing and expressing exogenous genes into cells and/or tissues are known in the art. For production of a "single protein" this system, a genetic construct (e.g., a cold-shock vector such as pColdI(SP4), pColdII(SP4), pColdIII(sp4), pColdIV, pColdI (W), pColdII(W), pColdIII(W); Vaiphei, et al. (2010) Appl. Eviron. Microbiol. 76:6063-6068) encoding the desired protein (i.e., the viroporin fragment) is engineered to transcribe an mRNA from which all of the mRNA interferase-target sequences (e.g., ACA) have been removed. This procedure generates an mRNA which is not susceptible to the endonuclease activity of the mRNA interferase added to the "single protein" expression system. Such an engineered mRNA transcript of the invention may be referred to herein as an "interferase resistant mRNA". Expression of an interferase resistant mRNA is carried out by inducing its expression from, for example, an engineered construct. Induction can be carried by conventional reagents including the use of isopropyl β-D-1-thiogalactopyranoside (IPTG). The interferase resistant mRNA is translated into protein, essentially in the absence of translation of any other proteins that are susceptible to the activity of the mRNA interferase, thus producing, in essence, a single protein sample.

By way of illustration, a portion of the gene encoding for M2 peptide (residues 1-49) and lacking the nucleotides 5'-ACA-3' was cloned into pColdII(sp4) and expressed in the single-protein-production system according to conventional practices. While the expression of this M2 peptide was not detected in the absence of amantadine, when amantadine (from 0.1 mM up to 2 mM) was added to the SPP culture medium, the M2(1-49) protein was expressed. This result indicated that M2(1-49) expressed by the SPP system formed an active ion channel in E. coli and that channel formation inhibited ATP production causing cell growth arrest thereby arresting further expression of M2(1-49). Moreover, this analysis indicated that any agent, which blocks the M2 channel, could induce the production of the M2 protein.

When carrying out the instant method of screening for an antiviral agent capable of blocking a viral viroporin, the expression of the viral viroporin fragment in a SPP system of *E. coli* is induced; the *E. coli* is contacted with a test compound; and it is determined whether the test compound rescues expression of the viral viroporin fragment. A compound that rescues expression of the viral viroporin by blocking its activity is a compound of use as an antiviral agent. Agents which can be screened in accordance with the instant assay can be rationally designed from crystal structure information or identified from a library of test agents. Test agents of a library can be synthetic or natural compounds. A library can comprise either collections of pure agents or collections of agent mixtures. Examples of pure agents include, but are not limited to, peptides, polypeptides, antibodies, oligonucleotides, carbohydrates, fatty acids, steroids, purines, pyrimidines, lipids, synthetic or semi-synthetic chemicals, and purified natural products, derivatives, structural analogs or combinations thereof. Examples of agent mixtures include, but are not limited to, extracts of prokaryotic or eukaryotic cells and tissues, as well as fermentation broths and cell or tissue culture supernatants. In the case of agent mixtures, one may not only identify those crude mixtures that possess the desired activity, but also monitor purification of the active component from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Subsequent to applying the test agent to the recombinant cell, it is determined whether the test agent modulates the expression of the viroporin fragment. While expression of the viroporin fragment itself can be detected as a readout in the instant assay (e.g., by COOMASSIE staining, silver staining, western blot analysis or dot blot analysis), in some embodiments, expression of the viroporin fragment is detected using a reporter protein. In accordance with this embodiment, nucleotide sequences encoding the reporter protein are inserted, in a separate operon, downstream of the nucleotide sequence encoding the viroporin fragment. In this fashion, only when the viroporin fragment is produced, i.e., in the presence of an agent that inhibits the ion channel, the reporter protein is also produced resulting in detectable reporter protein activity.

In the context of the present invention, a reporter protein is a protein that is readily detectable either by its presence, or by its activity, which results in the generation of a detectable signal. Reporter proteins which are detected based upon their activity, include, but are not limited to, reporter enzymes such as β-galactosidase (Nolan, et al. (1988) *Proc. Natl. Acad. Sci. USA* 85:2603-2607), chloramphenicol acetyltransferase (CAT; Gorman, et al. (1982) *Mol. Cell Biol.* 2:1044; Prost, et al. (1986) *Gene* 45:107-111), β-lactamase, β-glucuronidase and alkaline phosphatase (Berger, et al. (1988) *Gene* 66:1-10; Cullen, et al. (1992) *Methods Enzymol.* 216:362-368). The presence of the reporter enzyme can be measured via its enzymatic action on a substrate resulting in the formation of a detectable reaction product. For some enzymes, such as β-galactosidase, β-glucuronidase and β-lactamase, well-known fluorogenic substrates are available that allow the enzyme to covert such substrates into detectable fluorescent products.

A variety of bioluminescent, chemiluminescent and autofluorescent proteins, referred to herein as light-emitting reporter proteins, are also useful in the instant method. Exemplary light-emitting reporter proteins, which require a cofactor to emit light include, but are not limited to, the luciferase protein from firefly, *Photinus pyralis* (De Wet, et al. (1987) *Mol. Cell. Biol.* 7:725-737); the yellow fluorescent protein from *Vibrio fischeri* strain Y-1 which requires flavins as fluorescent co-factors (Baldwin, et al. (1990) *Biochemistry* 29:5509-15); the Peridinin-chlorophyll a binding protein from the dinoflagellate *Symbiodinium* sp. (Morris, et al. (1994) *Plant Mol. Biol.* 24:673:77); and the phycobiliproteins from marine cyanobacteria such as *Synechococcus*, e.g., phycoerythrin and phycocyanin (Wilbanks, et al. (1993) *J. Biol. Chem.* 268:1226-35).

In particular embodiments of the instant invention, the reporter protein is a light-emitting reporter protein that is an autofluorescent reporter protein. As used herein, an autofluorescent reporter protein is any protein capable of fluorescence when excited with appropriate electromagnetic radiation and does not require a cofactor or substrate to emit light. This includes fluorescent proteins whose amino acid sequences are either natural or engineered. Suitable autofluorescent reporter proteins for use in the instant invention include those from the green fluorescent protein (GFP) family of polypeptides, which are derived from the jellyfish species *Aequoria victoria*. A variety of useful Aequorea-related GFPs have been engineered by modifying the amino acid sequence of the naturally occurring GFP to create GFP mutants (Prasher, et al. (1992) *Gene* 111:229-233; Heim, et al. (1994) *Proc. Natl. Acad. Sci. USA* 91:12501-04; U.S. Pat. No. 5,625,048; PCT/US95/14692). Several basic classes of useful GFP mutants include red-shifted GFP, which has an emission peak around 511 nm but lacks the near-UV 395 nm excitation peak; blue fluorescent protein (BFP); cyan fluorescent protein (CFP); sapphire; and yellow fluorescent protein (YFP). See, e.g., Pollok and Heim (1999) *Trends Cell Biol.* 9:57-60. Fluorescent proteins from the sea pansy, *Renilla reniformis*, and *Phialidium gregarium* are also contemplated. See, Ward, et al. (1982) *Photochem. Photobiol.* 35:803-808; Levine, et al. (1982) *Comp. Biochem. Physiol.* 72B:77-85. The coding sequences for these autofluorescent reporter proteins are well-known in the art and can be used in the method of this invention.

What is claimed is:

1. A method for screening for an antiviral agent capable of blocking a viral viroporin comprising inducing expression of a viral viroporin fragment in a Single Protein Production system of *Escherichia coli* (*E. coli*);

contacting the *E. coli* with a test compound; and determining whether expression of the viral viroporin fragment is rescued, wherein rescue of the expression of the viral viroporin fragment indicates that the test compound blocks the viral viroporin.

2. The method of claim 1, wherein expression of the viral viroporin fragment is determined via a reporter protein.

* * * * *